United States Patent [19]
Moss

[11] Patent Number: 4,776,223
[45] Date of Patent: Oct. 11, 1988

[54] DOUBLE BEVEL CONSTRUCTION OF A DIAMOND ANVIL

[75] Inventor: William C. Moss, San Mateo, Calif.

[73] Assignee: The United States of America as represented by the United States Department of Energy, Washington, D.C.

[21] Appl. No.: 11,977

[22] Filed: Feb. 6, 1987

[51] Int. Cl.$^4$ .............. G01N 37/00; G01N 1/28; G01N 21/84
[52] U.S. Cl. .................. 73/864.91; 73/860; 425/77; 356/244; 356/36
[58] Field of Search ............ 73/864.91, 818, 860, 73/866, 432.1; 356/36, 244, 246; 425/77, DIG. 26

[56] References Cited

U.S. PATENT DOCUMENTS

| | | | |
|---|---|---|---|
| 3,079,505 | 2/1963 | Weir et al. | 425/DIG. 26 |
| 3,509,597 | 5/1970 | Kirk | 425/77 |
| 3,610,757 | 10/1971 | Valkenburg et al. | 356/244 X |
| 4,151,253 | 4/1979 | Waggoner et al. | 356/36 X |
| 4,339,252 | 7/1982 | Bell et al. | 425/DIG. 26 |
| 4,602,377 | 7/1986 | Schiferl et al. | 378/80 X |
| 4,715,711 | 12/1987 | Dunn | 356/410 X |

Primary Examiner—Tom Noland
Attorney, Agent, or Firm—Henry P. Sartorio; L. E. Carnahan; Judson R. Hightower

[57] ABSTRACT

A double or multiple bevel culet geometry is used on a diamond anvil in a high pressure cell apparatus to provide increased sample pressure and stability for a given force applied to the diamond tables. Double or multiple bevel culet geometries can also be used for sapphire or other hard crystal anvils. Pressures up to and above 5 Megabars can be reached.

4 Claims, 5 Drawing Sheets

DOUBLE BEVEL CONSTRUCTION OF A DIAMOND ANVIL

The United States Government has rights in this invention pursuant to Contract No. W-7405-ENG-48 between the U.S. Department of Energy and the University of California, for the operation of Lawrence Livermore National Laboratory.

FIELD OF THE INVENTION

This invention relates to construction of a diamond anvil, useful in high pressure materials research.

BACKGROUND OF THE INVENTION

U.S. Pat. No. 3,079,505, issued to Weir, Van Valkenberg and Lippincott, discloses a high pressure optical cell that allows direct viewing or monitoring of radiation transmitted through a material that is compressed at pressures up to 160 kbar. Two cylinders, each with a central cone section removed and a small central aperture therein, are used to align and hold two small faceted diamonds, with the sample between the diamonds, and to transmit controllable axial force to the diamonds and to the sample. Removal of a conical section produces a central aperture through which radiation is directed. The two cylinders apply force over an annulus on each diamond, and the pressure transmitted to the sample is non-uniform. To the extent that the diamonds are characterized or iillustrated (FIG. 3A of Weir et al), they appear to be unbeveled.

Kirk, in U.S. Pat. No. 3,509,597, discloses an improvement of the Weir et al invention, wherein natural diamonds may be used for one or both of the anvil diamonds, and a thick transparent disc of plate glass in contact with the diamonds is used to transmit pressure to the diamonds. The Kirk invention appears to allow use of smaller size diamonds of lower quality for the diamond anvil, but the patent figures and text do not indicate use of any culet configuration other than an unbeveled one.

A diamond anvil high pressure cell, useful for producing observable pressures up to 700 kbar, is disclosed by Bell and Mao in U.S. Pat. No. 4,339,252. The inventors note that use of an apertured steel gasket with two opposed diamonds forming, in combination, the sample cell was disclosed by or for the inventors in an earlier report in 1978. The diamonds shown for illustration (FIGS. 2 and 3 of the Bell/Mao patent) have truncated culets with single bevels.

SUMMARY OF THE INVENTION

One object of the invention is to provide improved diamond anvil cell apparatus to achieve sample pressures up to and above 5 Megabars (Mbars).

Another object is to provide improved diamond anvil cell apparatus that requires smaller applied force to achieve a given sample pressure and provide improved stability of the diamond anvil cell apparatus for a given sample cell pressure.

Other objects of the invention, and advantages thereof, will become clear by reference to the detailed description and the accompanying drawings.

To achieve the foregoing objects, in accordance with the invention, the method in one embodiment may comprise: a first diamond crystal, including a central flat surface of radius substantially 15–45 $\mu$m, a first bevel region of substantially annular shape of facets surrounding the central flat, with outer radius substantially 60–90 $\mu$m, and a second bevel region of substantially annular shape of facets surrounding the outer perimeter of the first bevel region, with outer radius substantially 120 $\mu$m or greater; a second diamond crystal substantially identical to the first diamond crystal; a planar sheet of high yield strength, ductile material with an aperture therein (containing the sample) of radius substantially 15–45 $\mu$m; and with the planes of the central flats of the two diamond crystals being parallel to one another and being spaced apart by substantially the thickness of the adjacent gasket material, and being positioned so that the central flat surfaces of the first and second diamond crystals and the perimeter of the planar sheet aperture form a substantially closed chamber. The two diamonds are positioned in the cell in a manner well known in the art. Addition of a second (or multiple) bevel to the crystal adjacent to the culet is a key feature of the invention.

In a second embodiment, first and second sapphire crystals may be substituted for the first and second diamond crystals, with the central flat surface having a radius of substantially 15–500 $\mu$m, the first bevel region having an outer radius of substantially 60–2500 $\mu$m, and the second bevel region having an outer radius of substantially 120 $\mu$m or greater.

DETAILED DESCRIPTION

In Rev. Mod. Phys. 55 (1983) 65–108 and in Scientific American 250 (April 1984) 54–62, Jayaraman notes that the diamond anvil cell can achieve static pressures of at least 1.7 Mbar for material behavior research; the current record is 5.5 Mbar. The diamond anvil cell has developed from the Bridgman anvil, circa 1905, and from subsequent improvements. The original Bridgman anvil used tungsten carbide for one or both of the pressure-producing surfaces and was opaque to visible wavelength radiation. In 1959, Weir, Lippincott, Van Valkenburg and Bunting, of the National Bureau of Standards, and, independently, Jamieson, Lawson and Nachtrieb, of the University of Chicago, fabricated the first diamond anvil cell devices for high pressure materials investigation.

Figure 1:
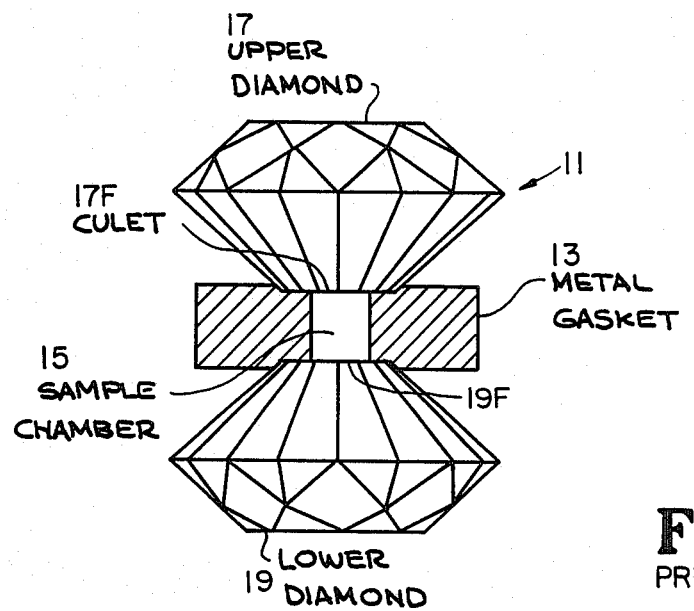
FIG. 1 is a perspective view of two representative unbeveled diamonds and gasket in a standard configuration.

With reference to FIG. 1, one prepares the cell 11 by pressing a predetermined area in a thin sheet 13 of metal or other suitable material, of initial thickness up to 250 micrometers (microns or $\mu m$), to a smaller thickness of no more than substantially 10–40 $\mu m$ and by drilling a small aperture 15 of radius substantially 15–45 $\mu m$ in the predetermined area of the sheet; the sheet material may be T-301 steel or rhenium or other high yield strength, ductile material. Each of two brilliant cut diamonds (0.1–0.5 carats) 17 and 19 has a small planar face or facet 17F and 19F of radius substantially 15–45 $\mu m$ on its truncated culet ("flat"). The sample to one studied is placed in the aperture 15 of the sheet, the culet of one diamond is positioned at the bottom of the aperture and the culet of the second diamond is positioned parallel thereto at the upper end of the aperture, with the sample positioned between these two culets. As the two diamonds are pressed together, the thin sheet 13 deforms around the diamonds and becomes a gasket, sealing off the sample contained in the aperture 15.

In one simple configuration, the central flats 17F and 19F may be initially spaced apart a distance $d_1 = 20–40$ $\mu m$, and the thickness $d_2$ of the prepressed sheet at the aperture may be slightly smaller than $d_1$. When the central flats 17F and 19F are pressed together so that the adjacent sheet material forms a tight gasket, sample pressures of one or more Mbars can be generated, often limited by the anvil geometry and its mechanical stability under such stresses.

Figure 2A:
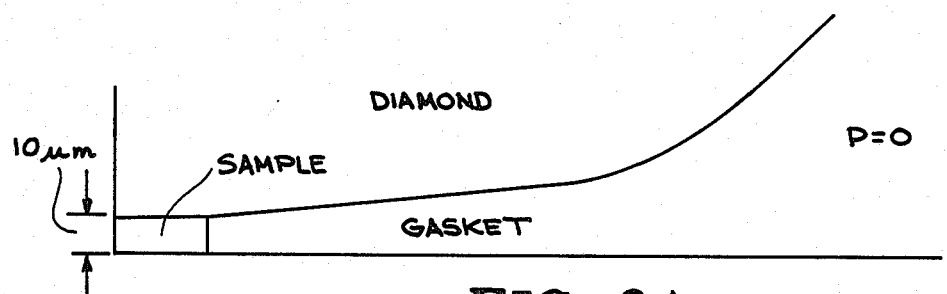
FIGS. 2(a) and 2(b) are sectional views of the deflection of the culet of single bevel (sb) and double bevel (db) anvils, calculated from finite element simulations. Experimental data for these configurations are also shown, by crosses. The notation used here is explained in the text.
Figure 2B:
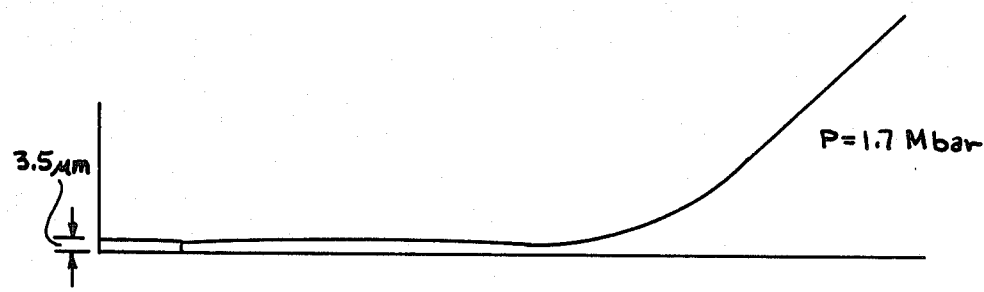

The inventor hereof has used finite element (FE) stress analysis to study and improve the bevel geometry (bevel angle(s), number of bevels, flat diameters, etc.) of a diamond anvil. The FE simulations show that for a typical unbeveled or single bevel (sb) configuration, the diamonds "cup" when the sample pressure becomes large. When the diamonds cup, large tensile stresses develop in the interior of the diamond. Further, when the cupped regions contact the gasket material, large tensile stresses also develop near the annular-contact region, and these contact stresses can cause failure of one or both of the diamonds. FIG. 2 shows the deflection of a diamond pressed against a gasketed sample. The diamond has a 25 $\mu m$ radius central flat and a 5° single bevel out to a radius of 150 $\mu m$. This single bevel geometry is denoted 25/5/150sb. The initial undeformed (sample pressure P = 0 Mbar) and cupped (P = 1.7 Mbar) configurations are shown in FIGS. 2(a) and 2(b), respectively.

Figure 3:
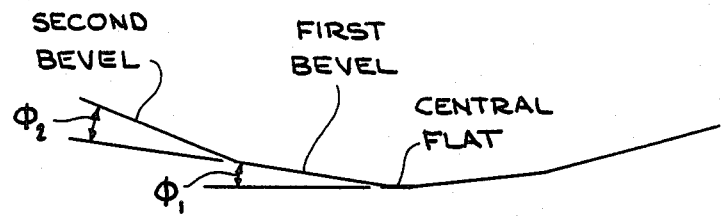
FIG. 3 is a sectional view of a double bevel diamond crystal suitable for practising the invention, showing the central flat and the first and second bevels.

If cupping can be prevented or delayed, higher sample pressures can be achieved, because the diamonds are less likely to fail when the tensile stresses therein are reduced. One way to delay the onset of cupping is to use a larger bevel angle, although it is well known experimentally that confining the sample and maintaining its stability becomes more difficult as the bevel angle increases. The FE simulations verify this observation: a sample could not be confined to produce a sample pressure of 1.7 Mbar, using a 25/8/150sb culet. Contact first occurs at the edge of the culet so that removing that region (shown as a shaded region in FIG. 2(b)) improves the performance. This removal may be accomplished by adding a second bevel to the undeformed diamond; and it still allows use of a modest first bevel angle so that the sample can be confined. A central flat is provided adjacent and contiguous to a first bevel having an angle ) ($\phi_1$) that is normally no more than 8°; and the first bevel region is adjacent and contiguous to a second bevel with a differential bevel angle ($\phi_2$) of no more than 5°, as illustrated in FIG. 3. Provision of double or multiple bevels for a diamond anvil is the key feature of this invention. The results of FE simulation, some of which are shown in FIGS. 4, 5, 6 and 7, indicate why the double bevel diamond anvil is superior to a single bevel or unbeveled diamond anvil.

Figure 4:
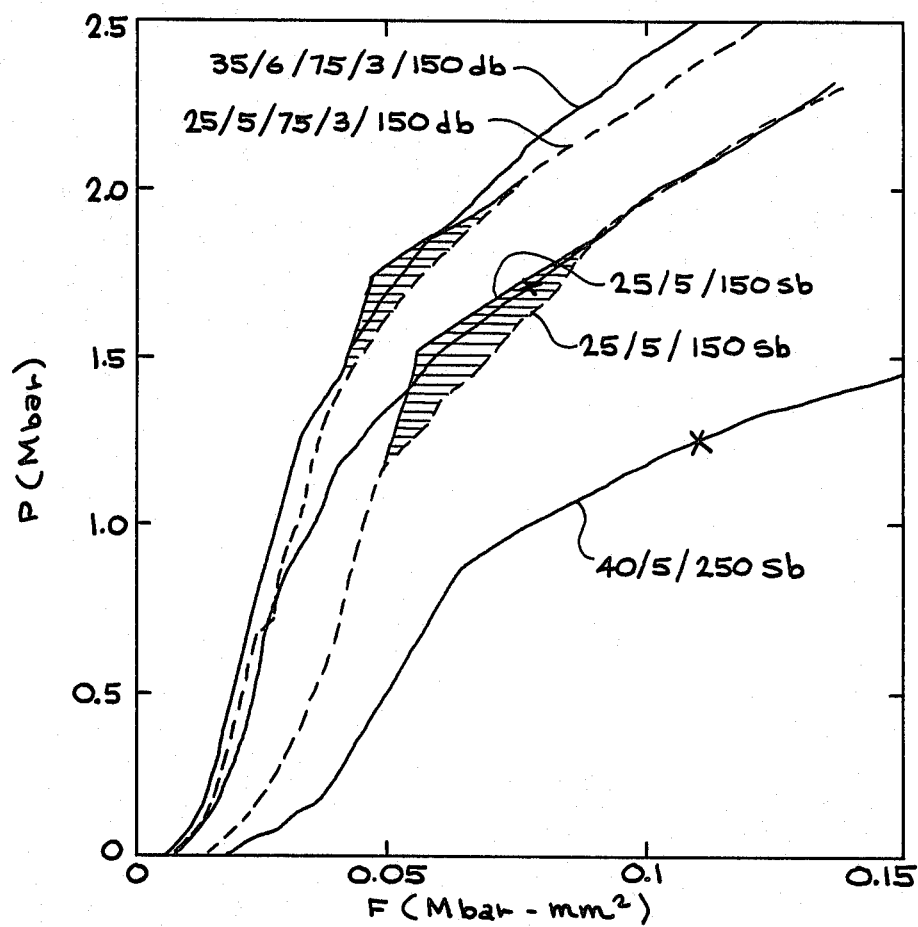
FIG. 4 graphically shows sample pressures, as a function of force applied to the diamond tables, for various single bevel (sb) and double bevel (db) anvils, calculated from finite element simulations; experimental data for two of these configurations are shown with crosses. The notation used here is explained in the text.

The thin solid lines in FIG. 4 exhibit the results of two FE simulations, and comparison with experiment, that have been performed on single bevel diamond anvil geometries: (1) 25 $\mu m$ radius central flat, 5° bevel angle and 150 $\mu m$ radius culet (denoted 25/5/150sb in FIG. 4); and (2) 40/5/250sb. The gasket material in each instance is hardened T-301 steel sheet, pressed to 20 $\mu m$ thickness; the sample chamber is filled with solid cesium iodide and the diamonds are each one-third carat. The calculations show that the sample and gasket are compressed and the bevel angle decreases, for both culet geometries, as the pressure increases. The abrupt change in slope of each curve corresponds approximately to the onset of large scale cupping of the culet, which occurs when the bevel angle has decreased to approximately 0°. Most of the additional load deforms the diamond in an annulus at the outer edge of the culet. The maximum pressures achieved in the two experiments are shown by crosses in FIG. 4. Both experiments failed slightly beyond the point of abrupt change in slope of the numerical simulation curves. This is consistent with the commonly used experimental criteria that diamonds fail at a point on the experimental P (sample pressure) versus F (table force) curve slightly beyond the point of abrupt change in slope. This comparison between experiments and the corresponding FE simulations for two very different culet geometries appears to validate use of the calculated P versus F curve to predict performance of a diamond anvil.

FIG. 4 also exhibits results of the FE analyses for two double bevel configurations: (1) 25 $\mu m$ radius central flat, 5° first bevel angle to 75 $\mu m$ radius, and an additional 3° second bevel angle to 150 $\mu m$ radius (denoted 25/5/75/3/150db in FIG. 4); and (2) 35/6/75/3/150db. These db curves indicate a 10–30 percent improvement, vis-a-vis the 25/5/150sb configuration, in sample pressure for a given table force, without sacrificing stability of the configuration. Viewed from another perspective, for a given target sample pressure, the applied table force is reduced and stability is improved.

The double bevel design 25/5/75/3/150db predicts 2.0 Mbar sample pressure for an applied table force of $7.5 \times 10^4$ r-mm$^2$, as compared with a predicted sample pressure of 1.7 Mbar for the same table force using the 25/5/150sb configuration. The 35/6/75/3/150db configuration performs even better, for the same applied table force. A 15/7/75/3/150db configuration, not shown in FIG. 4, is predicted to achieve 2.5 Mbar for the same applied table force as the preceding configurations; this is nearly a 50 percent improvement over the 25/5/150sb. design. In each of the configurations just discussed, the predicted maximum tensile stresses are approximatey equal. These stresses in the diamond are proportional to the applied table force and independent of culet geometry, assuming that the cupped regions of the anvils have not come into contact with each other. The radii for the central flat and for the transition from first bevel to second bevel may lie in the ranges 15–45 $\mu m$ and 60–90 $\mu m$, respectively; and the outer radius of the second bevel may be 120 $\mu m$ and greater. The first bevel angle and second differential bevel angle may lie in the respective ranges 3–8 degrees and 1–6 degrees.

Figure 5:
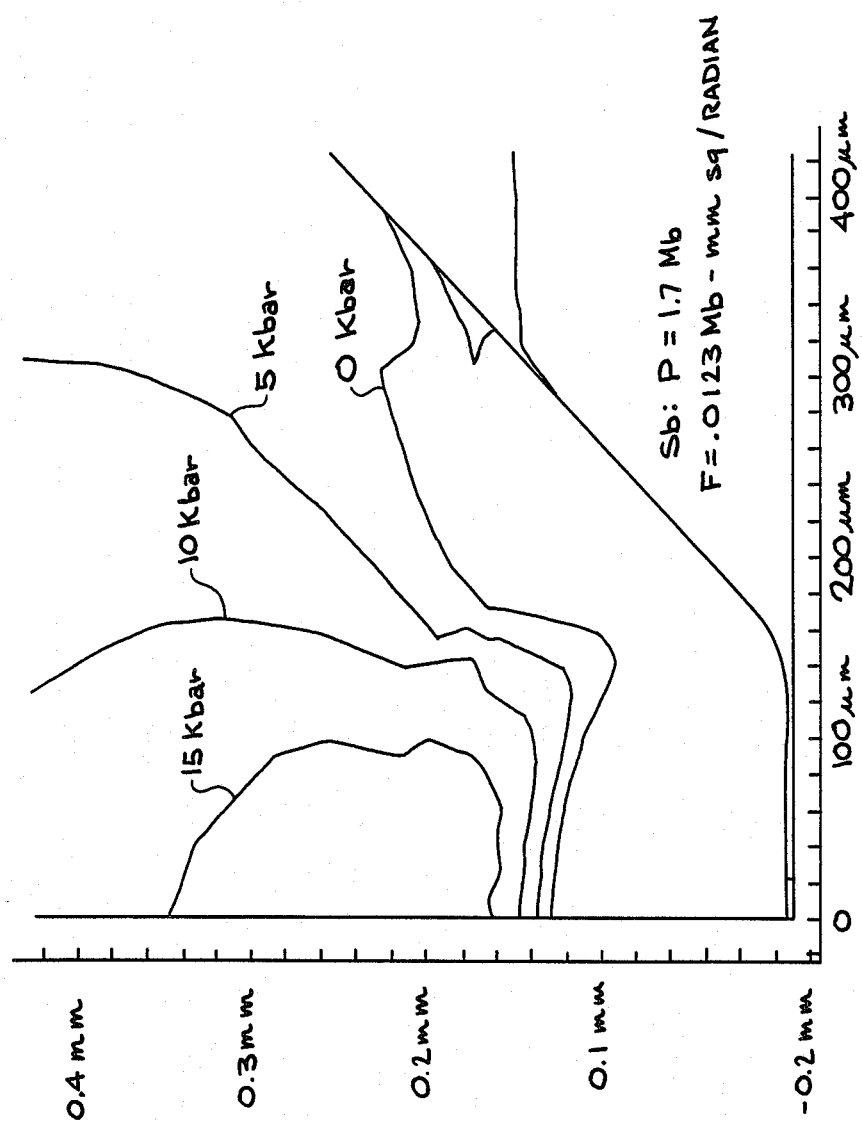
FIGS. 5, 6 and 7 show the deflections of a single bevel (FIG. 5) and a double bevel (FIGS. 6 and 7) diamond anvil, for sample pressures of 1.7, 2.0 and 1.7 Mbar, respectively; isostress contours of maximum principal tensile stress are also shown.
Figure 6:
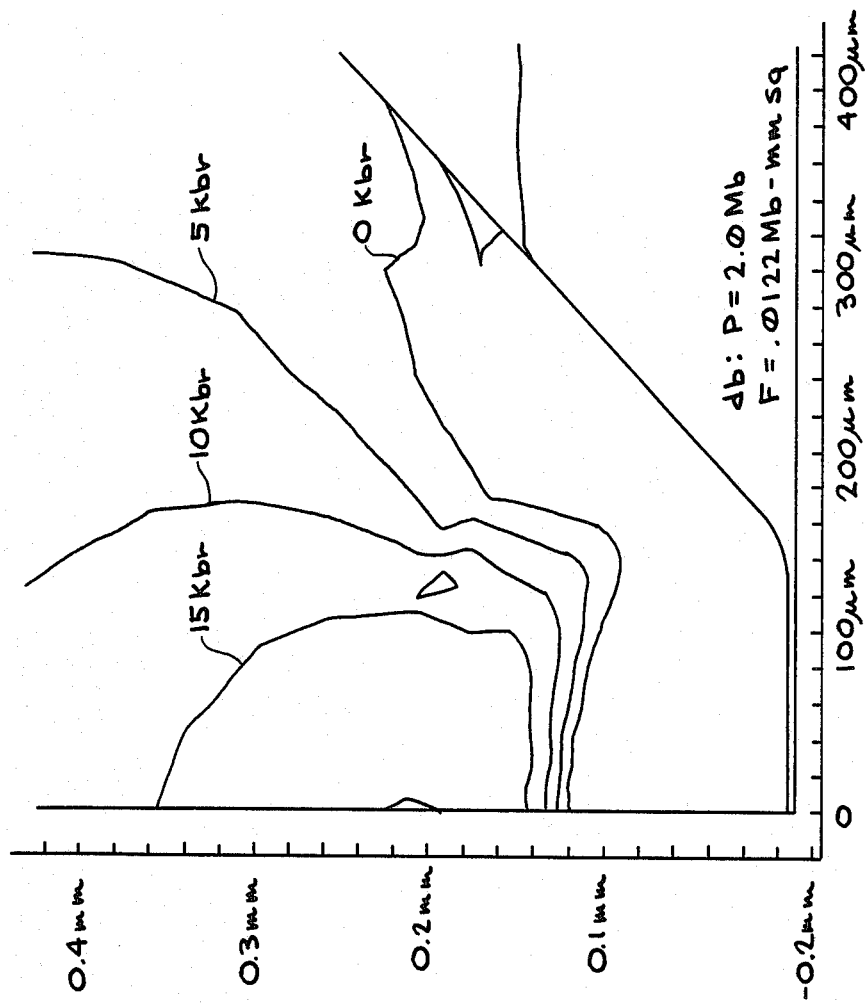
Figure 7:
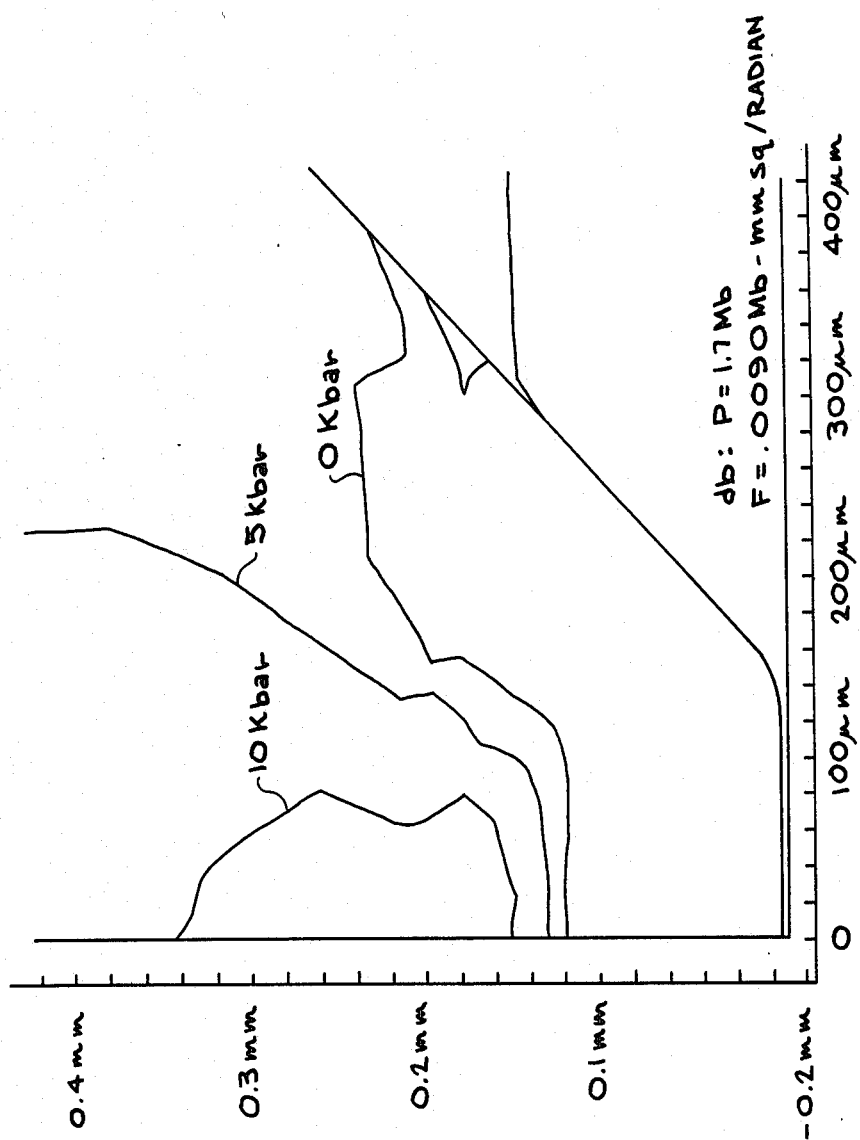

FIGS. 5, 6 and 7 indicate that the 25/5/75/3/150db configuration produces a higher sample pressure than the 25/5/150sb design, with comparable tensile stresses in the diamond; isostress contours of maximum principal stress for 0, 5, 10 and 15 kilobars are shown. The maximum tension in these FIGS. 5 and 6, for the given applied table forces, was approximately 30 kilobars, which is comparable with the tensile stress of diamond. Additionally, comparison of FIGS. 5 and 6 shows that the db configuration cups less than the sb configuration, for the same applied table force. Less cupping carries with it a smaller probability of diamond anvil failure, because it is less likely that the diamond culets will contact one another; in an actual experiment, the diamonds cannot be aligned perfectly as noted earlier, if the cupped diamonds contact one another, tensile stresses much larger than those in the interior of the diamonds are produced near the contact region and failure occurs. For comparison, FIG. 7 shows isostress contours of maximum principal stress for a sample pressure of 1.7 Mbar, using the 25/5/75/3/150db design. Note that the tensile stresses produced are significantly smaller than those produced in the sb design of FIG. 5, and no cupping occurs.

In preliminary experiments using the 35/6/75/3/150db design, a hydrogen sample achieved 2.1 Mbar sample pressure.

The preceding remarks also apply to the use of more than two bevels, referred to simply as multiple bevels herein. However, the most dramatic improvement should occur in the change from one to two bevel angles, for sample pressures that may be reached with a single bevel configuration. As one goes to sample pressures beyond those that can be reached with a single bevel angle design, cupping may occur where two bevel angles are used, and use of three or more bevel angles may be required.

The use of double or multiple bevels is not confined to diamond anvils; anvils of sapphire or other suitably-hard crystals should also exhibit increased performance with use of these configurations. In particular, sapphire offers a number of advantages over diamond: (1) larger crystals may be grown easily and inexpensively; (2) transmittance in the visible and near-infrared region is higher than 90 percent for sapphire but lower than 70 percent for diamond; and (3) the absorption edge for sapphire occurs at wavelengths of 144 nm and at wavelengths of 200 nm for Type II diamond. In "Sapphire-anvil Cell for High Pressure Research," Jap. Jour. of Appl. Phys. 25 (1986) 1646–1647, Furino, Onodera and Kume report use of sapphires with outer radii as large as 2500 $\mu$m and central flat radii as large as 500 $\mu$m, with unspecified single bevel angle. The plastic yield strength and ultimate tensile strength of sapphire are less than the corresponding parameters for diamond. Consequently, the ultimate sample pressures achievable using sapphire anvils will be less than those achieved using diamond. However, use of a double or multiple bevel configuration for sapphire snould allow sample pressures of about 0.5 Mbar and higher to be achieved, with much larger sample sizes than can be used with diamond.

Although the preferred embodiment of the invention has been shown and described herein, variation and modification may be made without departing from the scope of the invention.

I claim:

1. Improved diamond anvil apparatus, the apparatus comprising:
    a first diamond crystal, including a centrally positioned flat surface of radius substantially 15–45 $\mu$m, a first bevel region, of substantially annular shape, of facets with an associated first bevel angle, contiguous to and surrounding the perimeter of the flat surface, with outer annulus radius substantially 60–90 $\mu$m, and a second bevel region, of substantially annular shape, of facets with an associated second bevel angle, contiguous to and surrounding the outer perimeter of the first bevel region, with outer annulus radius substantially 120 $\mu$m or greater;
    a second diamond crystal, including a centrally positioned flat surface of radius substantially equal to the radius of the central flat surface of the first diamond crystal, a first bevel region, of substantially annular shape, of facets with an associated first bevel angle, contiguous to and surrounding the perimeter of the flat surface, with outer annulus radius substantially 60–90 $\mu$m, and a second bevel region, of substantially annular shape, of facets with an associated second bevel angle, contiguous to and surrounding the outer perimeter of the first bevel region, with outer annulus radius substantially 120 $\mu$m or greater;
    a planar sheet of high yield strength material, with an aperture in the sheet of radius substantially equal to the radius of the central flat surface in the first diamond crystal and with a sheet thickness of substantially 10–40 $\mu$m adjacent to the aperture; and
    with the planes of the flat surfaces of the two diamond crystals being oriented parallel to one another, being spaced apart by a distance substantially equal to the planar sheet thickness, and being positioned so that these flat surfaces and the perimeter of the planar sheet aperture form a substantially closed chamber.

2. Apparatus according to claim 1, wherein said first bevel angle of said first diamond crystal and said first bevel angle of said second diamond crystal are each substantially 3–8 degrees.

3. Apparatus according to claim 2, wherein said second bevel angle of said first diamond crystal and said second bevel angle of said second diamond crystal are each substantially 1–6 degrees.

4. Improved sapphire anvil apparatus, the apparatus comprising:
    a first sapphire crystal, including a centrally positioned flat surface of radius substantially 15–500 $\mu$m, a first bevel region, of substantially annular shape, of facets with an associated first bevel angle, contiguous to and surrounding the perimeter of the flat surface, with outer annulus radius substantially 60–2500 $\mu$m, and a second bevel region, of substantially annular shape, of facets with an associated second bevel angle, contiguous to and surrounding the outer perimeter of the first bevel region, with outer annulus radius substantially 120 $\mu$m or greater;
    a second sapphire crystal, including a centrally positioned flat surface of radius substantially equal to the radius of the central flat surface of the first sapphire crystal, a first bevel region, of substantially annular shape, of facets with an associated first bevel angle, contiguous to and surrounding the perimeter of the flat surface, with outer annulus radius substantially 60–2500 μm, and a second bevel region, of substantially annular shape, of facets with an associated second bevel angle, contiguous to and surrounding the outer perimeter of the first bevel region, with outer annulus radius substantially 120 μm or greater;

a planar sheet of high yield strength material, with an aperture in the sheet of radius substantially equal to the radius of the central flat surface in the first diamond crystal and with a sheet thickness of substantially 10–40 μm adjacent to the aperture; and with the planes of the flat surfaces of the two sapphire crystals being oriented parallel to one another, being spaced apart by a distance substantially equal to the planar sheet thickness, and being positioned so that these flat surfaces and the perimeter of the planar sheet aperture form a substantially closed chamber.

* * * * *